United States Patent
Patel et al.

(10) Patent No.: US 9,211,251 B2
(45) Date of Patent: *Dec. 15, 2015

(54) INJECTABLE PREPARATIONS OF DICLOFENAC AND ITS PHARMACEUTICALLY ACCEPTABLE SALTS

(71) Applicant: TROIKAA PHARMACEUTICALS LIMITED, Gujarat (IN)

(72) Inventors: Ketan Rajnibhai Patel, Gujarat (IN); Milan Rajnibhai Patel, Gujarat (IN)

(73) Assignee: TROIKAA PHARMACEUTICALS LIMITED, Gujarat (IN)

( * ) Notice: Subject to any disclaimer, the term of this patent is extended or adjusted under 35 U.S.C. 154(b) by 0 days.

This patent is subject to a terminal disclaimer.

(21) Appl. No.: 13/749,872

(22) Filed: Jan. 25, 2013

(65) Prior Publication Data

US 2013/0137769 A1 May 30, 2013

Related U.S. Application Data

(62) Division of application No. 11/883,331, filed on Jul. 30, 2007, now Pat. No. 8,809,393.

(51) Int. Cl.
  A61K 31/195 (2006.01)
  A61K 9/00 (2006.01)
  A61K 47/10 (2006.01)
  A61K 31/196 (2006.01)

(52) U.S. Cl.
  CPC ............. *A61K 9/0019* (2013.01); *A61K 31/196* (2013.01); *A61K 47/10* (2013.01)

(58) Field of Classification Search
  None
  See application file for complete search history.

(56) References Cited

U.S. PATENT DOCUMENTS 5,071,643 A * 12/1991 Yu et al. ............... 514/570
5,389,681 A *  2/1995 Galli .................... 514/567

* cited by examiner

*Primary Examiner* — Craig Ricci
(74) *Attorney, Agent, or Firm* — Baker Hostetler LLP; Tayan B. Patel, Esq.

(57) ABSTRACT

Injectable formulations of water-soluble salts of diclofenac, which cause significantly less pain at the site of injection and can be administered by intradeltoid route, in addition to intragluteal and slow intravenous route.

6 Claims, No Drawings

INJECTABLE PREPARATIONS OF DICLOFENAC AND ITS PHARMACEUTICALLY ACCEPTABLE SALTS

This is a divisional application U.S. application Ser. No. 11/883,331. Benefit of this nonprovisional application is hereby claimed in accordance with 35 USC 121.

FIELD OF THE INVENTION

The present invention relates to high concentration preparations of injectable diclofenac salts that are capable of being administered by intradeltoid route, over and above the intragluteal and slow intravenous route.

BACKGROUND

This is a divisional application U.S. application Ser. No. 11/883,331. Benefit of this nonprovisional application is hereby claimed in accordance with 35 USC 121.

Diclofenac is used, most commonly, as the sodium or Potassium salt for relief from pain and inflammation such as Musculoskeletal and joint disorders including rheumatoid arthritis, osteoarthritis, and ankylosing spondylitis. It is also useful in peri-articular disorders such as renal colic, acute gout, dysmenorrheal following surgical procedures. It has also been used in some countries for the management of fever.

British National Formulary recommends intramuscular injection into the gluteal muscle. Likewise, Martindale, the Extrapharmacopoea recommends intragluteal injections. The other route of administration, recommended is by IV infusion.

A typical parenteral administration is prepared by suspending or dissolving Sodium/Potassium salt of diclofenac in a non-toxic aqueous or oleaginous medium liquid vehicle.

Diclofenac injections have to be administered deep intramuscularly and are generally administered intraguluteally as the injection causes substantial pain at the site of injection and its administration in the deltoid (upper arm) region is generally avoided.

Pain at the site of injection is due to relatively large volume of the injection (3 mL) and the fact that the injection solution contains relatively high volumes of propylene glycol, which is a known irritant upon parenteral administration. As mentioned in Applied Nursing Research, Vol. 16, No. 2, August, 2002 empirical data from published research reports, recommendations of established advisory panels and generally accepted scientific principals conclude that only small volumes of medication (2 ml or less) should be given in the deltoid site. In fact, according to Nursing, January 1997, page 62-63, recommends the use of deltoid muscle only for volumes of 1 mL or less.

On the other hand intramuscular injection volumes above 2 ml and up to 5 ml must be administered into the gluteal muscle (Applied Nursing Research, Vol. 16, No. 2, August, 2002). This is because; the gluteal muscle is larger as compared to the deltoid muscle and hence can accommodate the relatively larger injected volume (3-5 ml). On the other hand if this relatively larger volume is injected into the deltoid muscle, which has relatively lesser muscle mass, the injected solution will cause excessive stretching of the muscle fiber, thereby damaging the local muscle tissue and hence cause pain and discomfort to the patient. (Svendsen and Blom, Arch. Toxicol, Suppl. 7, 1984)

Further, injectable diclofenac preparations contain relatively high amounts (18-40%) of propylene glycol, which is a known irritant. The Extra pharmacopoeia $28^{th}$ edition, Hand book of excipients, further reports that aqueous solution of 2% propylene glycol iso-osmotic with serum causes 100% haemolysis of erythrocytes in 45 min. (Martindale, the Extrapharmacopoea $28^{th}$ Edition).

Formulators have attempted to eliminate propylene glycol from the formulation in order to minimize pain at the site of the injection. It must be however be appreciated that the total volume of the injection solution plays a very significant role in addition to the amount of propylene glycol in the cause of pain at the site of the injection. As mentioned above, the volume of the injected solution causes stretching of the muscle fiber, and the higher the volume, more is the damage to the local muscle tissue and hence pain and discomfort at the site of injection.

U.S. Pat. No. 3,558,690 discloses injectable preparations comprising water soluble salts of substituted phenyl acetic acid derivatives (diclofenac being one such compound) in concentrations of 0.5 to 5%

Conventional diclofenac injections marketed as single dose ampoules, contain 75 mg diclofenac sodium in 3 mL aqueous solution (2.5%). Multi dose vials (30 mL) contain 750 mg in 30 mL solution (10 doses) are also being marketed.

PCT application number WO 9603121 A1 describes a antiphlogistic, analgesic, antipyretic parenteral preparation comprising diclofenac, its salt, or both, a surfactant, co-surfactant, water, at pH of 3-10 and optionally comprising an only component, that can exhibit sustained therapeutic levels of diclofenac in plasma and which does not cause pain at site of injection.

U.S. Pat. No. 5,554,650 discloses an antiphlogistic, analgesic, antipyretic parenteral preparation that can exhibit sustained therapeutic levels of diclofenac in plasma comprising diclofenac, its salt, or both, a surfactant, co-surfactant, water, adjusted to pH of 3-10 and optionally comprising an oily component. Some preparations claim not to cause pain at site of injection since they exclude propylene glycol and instead use a surfactant and co-surfactant or oil with surfactant and co surfactant to dissolve the diclofenac.

European Patent Application number 0658347 A3 describes a method of preparing an injectable pharmaceutical or veterinary composition, which comprises either diclofenac or a salt thereof, and 2 hydroxypropyl betacyclodextrin, or an inclusion complex of diclofenac or a salt thereof and 2 hydorxypropyle betacyclodextrin. Propylene glycol is excluded and solubilisation effected with the help of 2 hydroxypropyl betacyclodextrin.

The present inventions attempts to provide preparations of concentrated solutions of water soluble salts of diclofenac and reducing the overall volume of injection to 1 mL resulting in the minimization of pain at site of injection. Further, smaller volume enables administration in the deltoid muscle.

While incorporating 75-100 mg of water-soluble salts of diclofenac and reducing the volume of the injection solution from 3 ml to 1 mL, the viscosity of the injection solution can rise thereby hampering the ease of administration of the injection. It is therefore important to make judicious use of co-solvents/solubilisers, along with water to formulate injection solutions of water-soluble salts of diclofenac, to provide 75 mg to 100 mg in about 1 mL without substantially increasing the viscosity. Further it is also desirable to provide injectable preparations with low content of co-solvents/solubilisers to minimize their side effects.

SUMMARY OF THE INVENTION

The present invention provides injectable formulations of water-soluble salts of diclofenac, which cause significantly less pain at the site of injection and can be administered by intradeltoid route, in addition to intragluteal and slow intravenous route.

The present invention also provides single doses of less than 2 mL.

It is yet another object of the invention to provide injectable preparations containing 75 mg of water-soluble salts of diclofenac, in about 1 mL injection solution.

It is yet another abject of the invention to provide a full therapeutic dose of 75 mg to 100 mg of water-soluble salts of diclofenac in just one mL, without significantly raising the viscosity of the injection solution.

It is yet another object of the invention to provide an injectable preparation of water-soluble salts or diclofenac, without the use of surfactants, and preferably, a minimized quantity of co-solvents to avoid any possible side effects.

Thus in accordance of this invention, the formulations are adjusted to pH 6 to 10 containing up to 100 mg of diclofenac salt in a medium comprising of water, along with one or more co-solvent(s)/solubiliser(s), antioxidants, preservatives, buffers, alkali and stabilizers.

DETAILED DESCRIPTION OF THE INVENTION

It has surprisingly been found that co-solvent/solubilisers such as –4% to 85% v/v of monohydric alcohol, or –27% to 90% v/v of polyhydric alcohol, or –18% to 90% v/v of tetrahydrofurfuryl propylene glycol (glycofurol), in combination with water as principal solvent allows one to prepare injectables containing 75 mg to 100 mg of water-soluble salts of diclofenac in –4 mL injection solution;

Or, optionally, two or more of these co-solvents/solubilisers used in combination, up to –80% v/v monohydric alcohol and/or up to –85% v/v of polyhydric alcohol and/or up to –85% v/v of glycofurol (tetrahydrofurfuryl propylene glycol), along with water as principal solvent, allows one to prepare injectables containing 75 mg to 100 mg of water-soluble salts of diclofenac, in about 1 mL injection solution, with reduction in their individual concentrations.

A injectable preparations are prepared as follows:

Diclofenac sodium is suspended in a mixture of requisite quantities of glycofurol and say a monohydric alcohol and/or polyhydric alcohol in an inert environment, followed by addition of sterile water for injection, with stirring, followed by addition of a buffer and anti oxidant, then adjusting the pH to 8-9 using alkali which on further dilution with sterile water for injection to achieve the required concentration of 75 mg in 1 ml followed by sterilization either by sterile filtration or by autoclaving and filled in 1 ml ampoules flushed with inert gas prior to sealing. Optionally the final injectable solution is also filled 5/10 ml multi dose vials flushed with inert gas prior to sealing.

In addition to alkali metal salts of the active drug diclofenac, diethyl ammonium salts, and the like may also be used.

The monohydric alcohol are selected from benzyl alcohol, ethyl alcohol and the like, the polyhydric alcohols being selected from propylene glycol and their like including polyethylene glycols with molecular weight 300 to 600 Dalton, glycerin, 1,3-butylene glycol. Preferable polyethylene glycols include polyethylene glycol 300, polyethylene glycol 400 and polyethylene glycol 600. The other co-solvent or solubiliser used is glycofurol (tetrahydrofurfuryl propylene glycol).

Water-soluble salts of diclofenac are used in the range of 7.5% to 10% w/v.

The amount of monohydric alcohol, for example benzyl alcohol, when used as the sole co-solvent/solubiliser, may be incorporated in the range of about 4% to 25% v/v. However when used as co-solvent/solubiliser in combination with other co-solvents the amount of benzyl alcohol is up to about 10% v/v preferably reduced to about 4% v/v.

Polyhydric alcohol such as propylene glycol, when used as sole co-solvent/solubiliser maybe incorporated in the range of about 42% to 90% v/v. However when used as co-solvents/solubilisers in combination with other co-solvent/solubiliser, the amount is up to about 85% v/v.

The amount of polyethylene glycols, for example polyethylene glycol 400, when used as sole co-solvent is in the range of about 27% to 90% v/v. However, when used as co-solvent/solubiliser in combination with other co-solvent/solubilisers, the amount up to around 85% v/v.

The amount of tetrahydrofurfuryl propylene glycol (glycofurol), when used as sole co-solvent/solubiliser, maybe in the range of about 18 to 90% v/v. However when used as a co-solvent/solubiliser with other co-solvents/solubilisers, the amount is up to about 85% v/v.

The antioxidants are selected from sodium bisulphite, sodium meta bisulphite and their like, the alkali is selected form sodium hydroxide, potassium hydroxide and their like, and the buffer system is phosphate buffer, bicarbonate buffer and their like.

The invention is now described with a few non-limiting examples.

EXAMPLES

Example 1

A parenteral preparation containing diclofenac sodium 7.5% about 25% v/v glycofurol, about 3% v/v benzyl alcohol is prepared in an inert gas environment by suspending the diclofenac sodium in a mixture of requisite quantities of glycofurol and benzyl alcohol. Sterile water is added with constant stirring, followed by addition of phosphate buffer and sodium bisulphite and pH adjusted to 8-9 using sodium hydroxide. The solution is diluted with sterile water to achieve the required concentration of 75 mg in 1 mL. The entire process is carried out under inert gas environment. The ingredients may be mixed in any order. The resultant solution is sterilized either by sterile filtration or by autoclaving and filled in 1 mL ampoules flushed with inert gas prior to sealing. The resultant solution is also filled in 5/10 mL multi dose vials flushed with inert gas prior to sealing. The viscosity of the dose is 2.64 CPS measured using Oswald U Tube viscometer. The amount of co-solvents/solubiliser is 0.25 mL of glycofurol and 0.03 mL of benzyl alcohol, totaling to 0.28 mL per injected dose. As compared to this, the viscosity of the conventional 3 mL diclofenac injections, comprising 75 mg of diclofenac sodium, which contain 18 to 40% propylene glycol, is 2.1 to 5.5 CPS and the quantity of co-solvent propylene glycol is 0.54 mL to 1.4 mL per injected dose.

Example 2

A parenteral preparation containing diclofenac sodium 7.5% w/v. about 1% v/v of propylene glycol, 22% v/v of glycofurol, prepared as described in example 1. The viscosity of the dose is 2.23 CPS measured using Oswald U Tube viscometer. The amount of co-solvent/solubiliser is 0.01 ml of propylene glycol and 0.22 mL of glycofurol, totaling to 0.23 mL per injected dose.

Example 3

A parenteral preparation containing diclofenac sodium 10% w/v, about 25% v/v glycofurol, 4% benzyl alcohol, prepared in a manner described in Example 1. The viscosity of the dose is 2.95 CPS measured using Oswald U Tube viscometer. The amount of co-solvent/solubiliser is 0.25 mL of glycofurol and 0.04 ml of benzyl alcohol, totaling to 0.29 mL per injected dose.

Example 4

A parenteral preparation containing diclofenac sodium 7.5% w/v, about 13% v/v glycofurol, 4% benzyl alcohol, prepared in a manner described in Example 1. The final dosage contains. The viscosity of the does is 1.69 CPS measured using Oswald U Tube viscometer. The amount of co-solvent/solubiliser is 0.13 mL of glycofurol and 0.04 mL of benzyl alcohol, totaling to 0.17 mL per injected dose.

Example 5

A parenteral preparation containing diclofenac potassium 7.88% w/v. about 4% v/v of benzyl alcohol, 13% v/v of glycofurol, prepared as described in Example 1. The viscosity of the dose is 1.72 CPS measured using Oswald U Tube viscometer. The amount of co-solventisolubiliser is 0.04 mL of benzyl alcohol and 0.13 mL of glycofurol, totaling to 0.17 mL per injected dose.

Example 6

A parenteral preparation containing diclofenac diethyl ammonium 8.7% w/v. about 4% v/v of benzyl alcohol, 5% v/v of glycofurol, prepared as described in Example 1. The viscosity of the dose is 1.57 CPS measured using Oswald U Tube viscometer. The amount of co-solvent/solubiliser is 0.04 mL of benzyl alcohol and 0.05 mL of glycofurol, totaling to 0.09 mL per injected dose.

Example 7

A parenteral preparation containing diclofenac diethyl ammonium 8.7% w/v. about 4% v/v of benzyl alcohol, 2% v/v of glycofurol, 1% propylene glycol, prepared as described in Example 1. The viscosity of the dose is 1.59 CPS measured using Oswald U Tube viscometer. The total amount of co-solvent/solubiliser is 0.04 mL of benzyl alcohol, 0.02 mL of glycofurol and 0.01 mL of propylene glycol, totaling to 0.07 mL per injected dose.

Example 8

A parenteral containing diclofenac sodium 7.5% w/v. about 35% v/v of glycofurol, prepared as described in Example 1. The viscosity of the dose is 3.99 CPS measured using Oswald U Tube viscometer. The total amount of co-solvent/solubiliser is 0.35 mL per injected dose. In view of the fact that the concentration of the injection solution is three times that of the generally used concentration, sub-acute toxicity study was performed to ascertain that the injection solution was devoid of toxicity.

Example 9

A parenteral preparation containing diclofenac sodium 7.5% w/v. about 45% v/v of propylene glycol, prepared as described in Example 1. The viscosity of the dose is 4.38 CPS measured using Oswald U Tube viscometer. The total amount of co-solvent/solubiliser is 0.45 mL of per injected dose.

Example 10

A parenteral preparation containing diclofenac sodium 7.5% w/v. about 33% v/v of polyethylene glycol 400, prepared as described in Example 1. the viscosity of the dose is 4.69 CPS measured using Oswald U Tube viscometer. The total amount of co-solvent/solubiliser is 0.35 mL per injected dose.

In view of the fact that the concentration of the injection solution is three times that of the generally used concentration, sub-acute toxicity study was performed to ascertain that the injection solution was devoid of toxicity.

Sub-acute toxicity studies of diclofenac sodium 75 mL/mL injection for 4 weeks with weekly observations were performed at the L. M. Collage of Pharmacy, Department of Pharmacology, Ahmedabad, India. The dose as prepared in example 4 was chosen for the study. 16 healthy albino rabbits (8 males & 8 females) and 48 Healthy Wistar rats (24 males & 24 females) were chosen for the study. All animals were kept in isolated cages in air-conditioned animal house with standard light, humidity, diet and water supply.

Four groups 4×2 (each of six rats) and 4×2 (each of 2 rabbits) were created for the study.

Group 1 consisting of 6 male and 6 female rats was intravenously administered normal saline injections of volume of 0.1 mL/100 g body weight and for the 6 male and 6 female rabbit volume of 0.1 mUkg body-weight.

Group 2 consisting of 6 male and 6 female rats and 6 male and 6 female rabbits was administered 75 mg/mL Diclofenac sodium equivalent therapeutic intravenously in human dose i.e. 1.0 mg/kg body weight.

Group 3 consisting of 6 male and 6 female rats and 6 male and 6 female rabbits was administrated 75 mg/mL Diclofenac sodium equivalent therapeutic intravenously in human dose i.e. 5.0 mg/kg body weight.

Group 4 consisting of 6 male and 6 female rats and 6 male and 6 males rabbits was administered 75 mg/mL Diclofenac sodium equivalent therapeutic intravenously in human dose i.e. 10.0 mg/kg body weight.

Body weight, Food consumption, Water intake, including General examination and Biochemical Investigations such as Complete blood count, Serum Cholesterol, Serum Glucose, SGOT & SGPT, Serum Urea and Serum Creatinine were monitored weekly.

There was no significant difference in the growth or in the final body weight attained in all four test groups as compared to control (FIG. 1,2). Food intake was adequate indicating no change in the appetite (FIG. 3,4). Water intake was also not significantly different in test animals as compared to control (FIG. 5,6). Activity of animals was normal and there were no apparent features of stimulation or depression noted.

Serum glucose, serum cholesterol, serum GOT, serum GPT or serum urea levels measured in rats and rabbits were not found to be significantly altered in any of the test groups as compared to control. Serum Creatinine was also not altered in any group except in rats treated with 1 Omekg. This dose did not produce any significant change in Creatinine levels in rabbits. Hostopathological examination of all the organs and the microscopic examination of liver, kidney, lung and heart did not reveal any apparent change except for degenerative changes observed in liver obtained from rabbit treated with 5 mg/kg and 10 mg/kg diclofenac sodium. The changes in liver have already been reported for diclofenac per se (Helfgott et al. 1990. JAMA, 264:20; Roque et al. 1999. Pharmacol. Experimental Thera, 288: 65-72). The adjuvants used in the formulations do not be produce any toxic effect in the animals studied.

The study suggests that treatment of diclofenac sodium injection has no undue toxicity as compared to the negative control.

What is claimed is:

1. An injectable preparation comprising:
   (A) at least one water-soluble salt of diclofenac (75 mg);
   (B) a single co-solvent selected from the group consisting of:
      a monohydric alcohol (4% to 25% v/v) selected from the group consisting of benzyl alcohol and ethyl alcohol,
      a polyhydric alcohol (27% to 45% v/v) selected from the group consisting of propylene glycol, polyethylene glycols having a molecular weight of between 300 to 600 Dalton, glycerin, and 1,3-butylene glycol, and
      glycofurol (18% to 35% v/v),
      in combination with water;
   (C) an alkali selected from the group consisting of sodium hydroxide and potassium hydroxide; and
   (D) a buffer system selected from the group consisting of phosphate buffer and bicarbonate buffer;
   wherein the viscosity of the preparation ranges from 1.50 to 4.7 centipoise (CPS); the final volume of the injectable solution is approximately 1 ml; the pH of the injectable solution is maintained at between 8 and 9 by said alkali and said buffer system; and the injectable solution is capable of being administered by the intradeltoid, intragluteal route, and/or slow intravenous route.

2. An injectable preparation of diclofenac and its pharmaceutically accepted salts as high concentration preparations according to claim 1, wherein the said water-soluble salts of diclofenac is selected from a group comprising of alkali metal salts and diethyl ammonium salts.

3. An injectable preparation of diclofenac and its pharmaceutically accepted salts as high concentration preparations according to claim 1, wherein the polyhydric alcohol is selected from a group comprising of polyethylene glycol 300, polyethylene glycol 400, and polyethylene glycol 600.

4. An injectable preparation of diclofenac and its pharmaceutically accepted salts as high concentration preparations according to claim 1, wherein said polyhydric alcohol is propylene glycol.

5. An injectable preparation of diclofenac and its pharmaceutically accepted salts as high concentration preparations according to claim 1, wherein said single co-solvent is glycofurol.

6. A medicament comprising the injectable preparation of diclofenac and its pharmaceutically accepted salts as high concentration preparations according to claim 1.

* * * * *